United States Patent [19]

Seeney

[11] Patent Number: 5,449,494
[45] Date of Patent: Sep. 12, 1995

[54] SAMPLING DEVICE

[75] Inventor: Philip Seeney, Cambridge, United Kingdom

[73] Assignee: Amersham International plc., Buckinghamshire, United Kingdom

[21] Appl. No.: 170,231
[22] PCT Filed: Jun. 30, 1992
[86] PCT No.: PCT/EP92/01480
  § 371 Date: Feb. 14, 1994
  § 102(e) Date: Feb. 14, 1994
[87] PCT Pub. No.: WO93/00994
  PCT Pub. Date: Jan. 21, 1993

[30] Foreign Application Priority Data

Jul. 2, 1991 [GB] United Kingdom ............... 9114265

[51] Int. Cl.$^6$ ............................................. B01L 3/00
[52] U.S. Cl. ........................... 422/100; 422/102; 422/103; 73/864.51; 239/33
[58] Field of Search ............... 422/100, 102, 103; 73/864.51; 239/33

[56] References Cited

U.S. PATENT DOCUMENTS

| | | | |
|---|---|---|---|
| 3,464,800 | 9/1969 | Gerande | 422/100 |
| 3,715,189 | 2/1973 | Nighohossian et al. | 422/102 |
| 4,214,874 | 7/1980 | White | 422/100 |
| 4,324,758 | 4/1982 | Eisentraut et al. | 422/61 |
| 4,346,613 | 8/1982 | Turner et al. | 73/864.51 |
| 5,268,148 | 12/1993 | Seymour | 422/101 |
| 5,273,907 | 12/1993 | Malmquist | 436/165 |
| 5,330,899 | 7/1994 | De Vaughn | 435/30 |
| 5,334,348 | 8/1994 | Saito et al. | 422/61 |

Primary Examiner—Robert J. Warden
Assistant Examiner—N. Bhat
Attorney, Agent, or Firm—Wenderoth, Lind & Ponack

[57] ABSTRACT

A sampling device includes a cylindrical tube having a smaller diameter portion in which a plunger is mounted for sliding sealing movement. The inner end of the cylinder is sealed from the interior of the tube by a rupturable element, and the plunger has sharp end edge which will rupture the sealing element when the plunger is depressed. The outer end of the plunger is formed with a series of grooves capable of retaining a sample. Depression of the plunger breaks the sealing element and carries the sample into the tube to test its reaction with a reagent previously sealed in the tube. The end of the plunger remote from the sealing element forms a seal in the cylinder. A generally similar arrangement at the opposite end of the tube allows a second reagent to be added to the reagent in the tube.

6 Claims, 1 Drawing Sheet

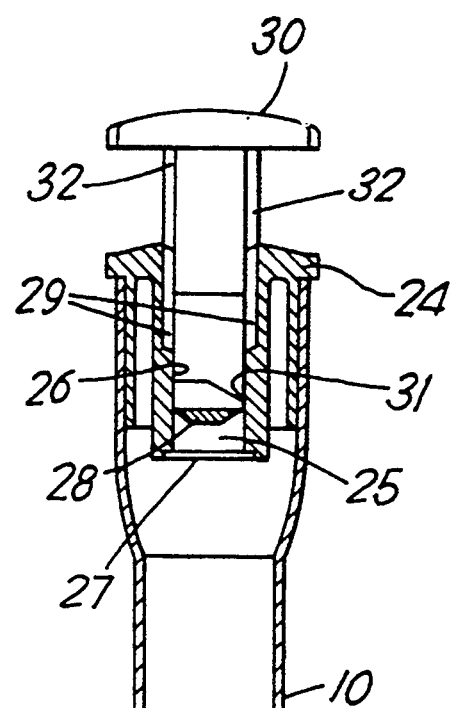
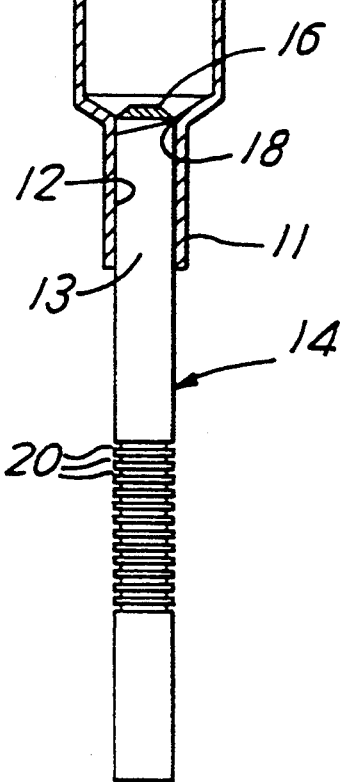
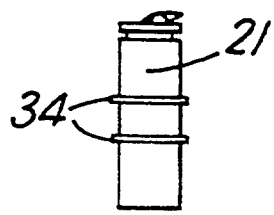
FIG.1
FIG.2

SAMPLING DEVICE

BACKGROUND AND SUMMARY OF THE INVENTION

This invention relates to sampling devices.

According to the present invention there is provided a sampling device comprising a closed reaction vessel, and a cylinder formed integrally with a wall of the vessel and having a bore in which a plunger is mounted for sliding sealing movement, the inner end of the bore being sealed from the interior of the vessel by a sealing element capable of being ruptured by the application of force against the sealing element by the plunger, part of the plunger projecting externally from the bore and having on its surface means for holding a predetermined quantity of a sample, and the arrangement being such that said part of the plunger carrying the sample can by depression of the plunger be moved into the interior of the vessel.

According to a preferred feature of the invention said means for holding a predetermined quantity of a sample comprises one or more holes or recesses in the plunger. In a preferred arrangement, said means for holding a predetermined quantity of a sample comprises a plurality of circumferential groves in the plunger, in which grooves a predetermined quantity of a sample can be retained by surface tension.

According to another preferred feature of the invention, the plunger is adapted to seal the bore when the said part is disposed in the interior of the vessel. For this purpose, the end portion of the plunger remote from the vessel may be of divergent cross-section, or may have one or more circumferential sealing ribs, so as to be capable of forming a tight seal in said bore when the said part of the plunger is disposed within the interior of the vessel.

According to a further preferred feature of the invention, the vessel has at least one chamber in the wall thereof which chamber is isolated from the interior of the vessel by a first seal and from the ambient surroundings by a second seal and which is intended to contain a reagent, and a second plunger mounted in a bore in a second cylinder on the wall of the chamber which plunger is operable to rupture said second and first seals in succession and serves then to seal the chamber (and in consequence the interior of the vessel) from the ambient surroundings.

BRIEF DESCRIPTION OF THE DRAWINGS

One embodiment of the invention will now be described by way of example with reference to the accompanying drawings in which:

FIG. 1 is a longitudinal sectional view of a sampling device according to the invention, and FIG. 2 illustrates a modification of a plunger of the device.

Referring to the drawings, a cylindrical tube molded from a plastics material such as polypropylene affords a vessel 10 and has at one axial end thereof a reduced diameter portion forming a cylinder 11 in the bore 12 of which one end portion 13 of a plunger 14 is slidingly and sealingly mounted. The end of the bore 12 adjoining the interior of the vessel is formed with an integral sealing element 16, and the inner end of the plunger is cut so as to form a sharp edge 18 capable of rupturing the seal. The middle part of the plunger projecting from the bore is formed with a series of shallow circumferentially extending grooves 20 which are adapted to hold a predetermined small quantity of a sample, using surface tension properties. The free end portion 21 of the plunger further from the vessel is slightly divergent so that when the plunger is depressed to rupture the seal and to carry the sample in the grooves into the interior of the vessel, the end portion 21 of the plunger forms a tight seal in the bore 12.

The opposite end of the cylindrical tube is closed off by an annular plug 24 molded from a plastics material such a polypropylene and having a central bore 26. The end of the bore adjoining the interior of the vessel is sealed by a rupturable sealing diaphragm 27, and spaced along the bore from the diaphragm is a second rupturable sealing element 28 which is moulded integrally with the plug. A sealed chamber 25 formed between the diaphragm 27 and element 28 may contain a reagent. The axially outer end portion of the bore in the plug is formed with two diametrically opposite key-ways 29. A plunger 30 slidingly and sealingly mounted in the bore has its end 31 adjoining the integral seal sharpened so as to be capable of rupturing the integral seal 28 and the diaphragm 27, and has its axially outer portion formed with keys 32 capable of engaging in the key-ways in the bore. Thus the plunger can only be depressed to rupture the integral seal 28 and the diaphragm 27 when its keys are aligned with the key-ways 29 in the bore. This prevents accidental depression of the plunger.

In the modification illustrated in FIG. 2, the free end portion 21 of the plunger is formed with two circumferential sealing ribs 34 instead of being divergent as in the arrangement of FIG. 1.

In one mode of using the device, a quantity of a reagent is placed in the tubular vessel 10, the plunger 14 is immersed in a solution containing a sample and the solvent allowed to evaporate leaving the sample dried on the grooved area of the plunger. The plunger may first need to be treated with an appropriate reagent (e.g. a surfactant) before it can pick up the sample, but the first reagent and the surfactant may be one and the same. A precise volume of the sample is drawn up by surface tension onto the externally grooved region of the plunger. This volume can be carefully controlled in forming the grooves in manufacture and may be as large as necessary. In typical examples, the volume of the sample is 50 ul.

As the sample makes contact with the first reagent, the first chemical reaction occurs. The time of reaction can be as long as necessary. When sufficient reaction time has elapsed, the plunger 14 is depressed to rupture the seal, to convey the grooved area of the plunger into the interior of the vessel and to cause the divergent or, as the case may be, ribbed end portion 21 of the plunger to form a tight seal in the bore. The secondary reagent in the interior of the vessel can react with the product of the first reaction or any remaining unused first reagent. The time for this reaction can also be as long as necessary. After this reaction, if further processing is required the contents of the chamber 25 can be added to the contents of the vessel by operation of the second plunger 30 to initiate a further reaction, by inversion if necessary.

It will therefore be understood that the illustrated device enables a series of reactions to be carried out without further dispensing or dilution or other treatments. Additionally, the device will fit into many detection instruments such as luminometers.

I claim:

1. A sampling device comprising a closed reaction vessel, a cylinder integral with a wall of the vessel and having a bore, a cylindrical plunger mounted in said bore for sliding sealing movement, and a sealing element sealing an inner end of the bore, said sealing element capable of being ruptured by an end of the plunger nearest to said sealing element, the cylindrical surface of the plunger forming a seal with the bore, and the plunger having a portion which projects axially from the bore when the plunger is in a non-depressed position, the outer cylindrical surface of said projecting portion of the plunger having holding means for holding a predetermined quantity of a sample, and the device being dimensioned such that by pressing the projecting portion of the plunger into the bore a sample held by said holding means will be moved past the sealing element into the interior of the vessel, the bore remaining sealed by the plunger.

2. A sampling device as claimed in claim 1, wherein said means for holding a predetermined quantity of a sample comprises a plurality of circumferential grooves in the plunger, in which grooves a predetermined quantity of the sample can be retained by surface tension.

3. A sampling device as claimed in claim 1, wherein the end portion of the plunger remote from the vessel has a cross section that increases in a direction away from said vessel so as to form a tight seal in said bore when said projecting portion of the plunger is disposed within the interior of the vessel.

4. A sampling device as claimed in claim 1, wherein the end portion of the plunger remote from the vessel has one or more circumferential sealing ribs adapted to form a tight seal in said bore when the projecting portion of the plunger is disposed within the interior of the vessel.

5. A sampling device as claimed in claim 1, wherein the vessel has at least one chamber in the wall thereof and which chamber includes a first seal isolating said chamber from the interior of the vessel and a second seal isolating said chamber from the ambient surroundings, and further comprising a second cylinder disposed on said chamber, and a second plunger mounted in a bore in said second cylinder and which second plunger is operable to rupture said second and first seals in succession and serves then to seal the chamber and consequently the interior of the vessel from the ambient surroundings.

6. A sampling device as claimed in claim 1, wherein the vessel is tubular and said cylinder forms a tubular continuation of the tubular vessel.

* * * * *